United States Patent
Kirakossian

(10) Patent No.: US 8,679,764 B2
(45) Date of Patent: Mar. 25, 2014

(54) DENSITY-BASED CELL DETECTION SYSTEM

(75) Inventor: Hrair Kirakossian, San Jose, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 942 days.

(21) Appl. No.: 12/380,877

(22) Filed: Mar. 3, 2009

(65) Prior Publication Data

US 2010/0068754 A1  Mar. 18, 2010

Related U.S. Application Data

(60) Provisional application No. 61/069,078, filed on Mar. 11, 2008.

(51) Int. Cl.
  *G01N 33/50* (2006.01)
  *G01N 9/36* (2006.01)
  *G01N 15/04* (2006.01)

(52) U.S. Cl.
  CPC .......... *G01N 9/36* (2013.01); *G01N 15/042* (2013.01); *C12Q 2563/155* (2013.01)
  USPC ........................................ 435/7.1

(58) Field of Classification Search
  CPC ... G01N 15/042; G01N 9/36; C12Q 2563/137
  USPC ........................................ 435/7.1
  See application file for complete search history.

(56) References Cited

U.S. PATENT DOCUMENTS

| 4,920,061 A | 4/1990 | Poynton et al. |
| 5,342,790 A | 8/1994 | Levine et al. |
| 5,550,060 A * | 8/1996 | Saunders et al. ............... 436/63 |

(Continued)

FOREIGN PATENT DOCUMENTS

| EP | 1852702 | 11/2007 |
| WO | 199524631 | 9/1995 |
| WO | 199852040 | 11/1998 |
| WO | 2004011941 | 2/2004 |

OTHER PUBLICATIONS

Bikoue et al., "Quantitative Analysis of Leukocyte Membrane Antigen Expression: Normal Adult Values"; Cytometry (Communications in Clinical Cytometry) 26:137-147 (1996).

(Continued)

*Primary Examiner* — Bao Thuy L Nguyen
*Assistant Examiner* — Pensee Do
(74) *Attorney, Agent, or Firm* — Bozicevic, Field & Francis LLP; Bret E. Field; James S. Keddie

(57) ABSTRACT

The invention provides a low-cost method for identifying and/or measuring a subpopulation of cells in a biological sample, such as a subpopulation of CD4-positive cells in a whole blood sample. In accordance with the invention, one or more cell surface markers are identified on a subpopulation of interest, which collectively are present in higher numbers on the cells of the subpopulation than on cells not in the subpopulation of interest. A probe comprising a binding compound and a density label are combined with the sample and the resulting mixture is centrifuged or sedimented through a density medium in a capillary. Labeled cells of interest pass through the density medium and stack at the bottom of the capillary where they may be visually detected and quantified by the height of the stack.

9 Claims, 4 Drawing Sheets

(56) References Cited

U.S. PATENT DOCUMENTS

| | | | |
|---|---|---|---|
| 5,840,502 | A | 11/1998 | Van Vlasselaer |
| 5,974,901 | A * | 11/1999 | Zborowski et al. .......... 73/865.5 |
| 7,316,932 | B2 * | 1/2008 | Woodside .................... 436/177 |
| 2003/0147886 | A1 | 8/2003 | Thomas et al. |
| 2009/0148869 | A1 | 6/2009 | Zaugg et al. |

OTHER PUBLICATIONS

Bildirici et al., "Fractionation of differentiating cells using density perturbation"; Journal of Immunological Methods 240 (2000) pp. 93-99; www.elsevier.nl/locate/jim.

Nouanthong et al, "A Simple Manual Rosetting Method for Absolute CD4+ Lymphocyte Counting in Resource-Limited Countries"; Clinical and Vaccine Immunology, May (2006) vol. 13, No. 5, pp. 598-601;

Patel et al., "Use of density perturbation to isolate immunology distinct population of cells", Journal of Immunological Methods, 163 (1993) pp. 241-251.

Ribrioux et al., "Use of Nanogold- and Fluorescent-labeled Antibody Fv Fragments in Immunocytochemistry"; The Journal of Hostochemistry and Cytochemistry (1996) vol. 44, No. 3, pp. 207-213.

Rodriguez et al., "A Microchip CD4 Counting Method for HIV Monitoring in Resource-Poor Settings"; PLoS Medicine; Jul. (2005) vol. 2, Issue 7 pp. 0663-0672.

"Rosette SEP Procedure, Human CD4=T Cell Enrichment Cocktail" [Online internet citation] XP002408216; URL:http://www.stemcell.com/technica1/15022_15062_PIS.pdf> (Retrieved Nov. 11, 2006).

Schmitz et al., "Optimizing follicular dendritic cell isolation by discontinuous gradient centrifugation and use of the magnetic cell sorter (MACS)"; Journal of Immunological Methods, 159 (1993) pp. 189-196.

"CD4+ T-Cell Enumeration Technologies, Technical Information"; World Health Organization; UNAIDS; (2004) 7 pp.

* cited by examiner

DENSITY-BASED CELL DETECTION SYSTEM

CROSS-REFERENCE

This application claims the benefit of U.S. Provisional Application No. 61/069,078, filed Mar. 11, 2008, which application is incorporated herein by reference.

BACKGROUND

The majority of HIV-infected people live in resource-poor regions where instruments critical for detecting, staging, and monitoring the disease condition resulting from HIV are frequently unavailable because of difficult field conditions, cost, or lack of trained personnel, e.g. Cohen, AIDS, Suppl 4: S81-S87 (2007). This has led to the development by several groups of low-cost instrumentation designed for deployment in resource-poor settings for measuring CD4 counts in patient blood samples, e.g. Rodriguez et al, PLoS Medicine, 2(7): e182 (2005); Ymeti et al, Cytometry A 71: 132-134 (2007); Cheng et al, Lab Chip, 7(2): 170-178 (2007); Pattanapanyasat et al, Clinical Cytometry, 72B: 387-396 (2007); and the like. Although such advances have reduced costs of cell counting techniques, generally all of these approaches still require detection or sample handling systems that either have dedicated electronic or optical components needing trained operators, calibration, or external power, or other drawbacks, or still do not reduce costs to levels permitting widespread applicability.

In view of the above, several medical and biotechnology fields would be significantly advanced with the availability of techniques, capable of point-of-care operation, which permitted facile and flexible measurements of cellular markers, particularly in biological fluids, such as blood.

SUMMARY OF THE INVENTION

The invention provides a low-cost and convenient method for detecting certain cell types in a sample by separating them from other cell types using density labels, such as gold particles. In one aspect, the invention provides a method for detecting a subpopulation of cells in a sample, wherein cells of the subpopulation have characteristic numbers of one or more cell surface markers, comprising the following steps: (a) combining under probe-binding conditions a sample with a probe comprising at least one binding compound specific for at least one of the one or more cell surface markers and a particle having a size and a composition, thereby forming a reaction mixture containing labeled cells from the subpopulation and other cells, wherein the one or more cell surface markers are present in greater numbers on cells of the subpopulation than on other cells of the sample and wherein the one or more cell surface markers, and the particle size and composition are selected so that labeled cells of the subpopulation have a density that is greater than that of other cells of the sample; (b) separating labeled cells of the reaction mixture through a density medium, the labeled cells of the subpopulation being denser than the density medium and the other cells of the sample being less dense than the density medium, so that the labeled cells of the subpopulation are separated from the other cells; and (c) detecting the subpopulation of cells in the density medium.

In another aspect, such method further provides a step of separating the reaction mixture through said density medium disposed in a capillary having a bottom, so that said labeled cells from the subpopulation form a stack having a height from the bottom of the capillary, wherein the height of the stack is monotonically related to the number of cells of the subpopulation in said sample. An exemplary, density medium is Histodenz™, or like media. Preferably, in such aspect, the stack of cell can be seen with the unaided eye. In further preference, the density medium is colored with a contrasting color to that of the density label, so that visualization of the stack is enhanced whenever the stack of cells displaces the density medium at the bottom of the capillary.

In another aspect, the invention provides kits for practicing the method of the invention, wherein such kits include a cuvette comprising a chamber with an inlet for introducing a sample and a capillary tube or channel loaded with a density medium. Optionally, such cuvette may include pre-loaded probes with density labels. Alternatively, kits of the invention may include one or more vials of reagents including probes, such that probes are mixed with a sample and then the resulting mixture is loaded into the cuvette.

DETAILED DESCRIPTION OF THE INVENTION

Figure 1A:
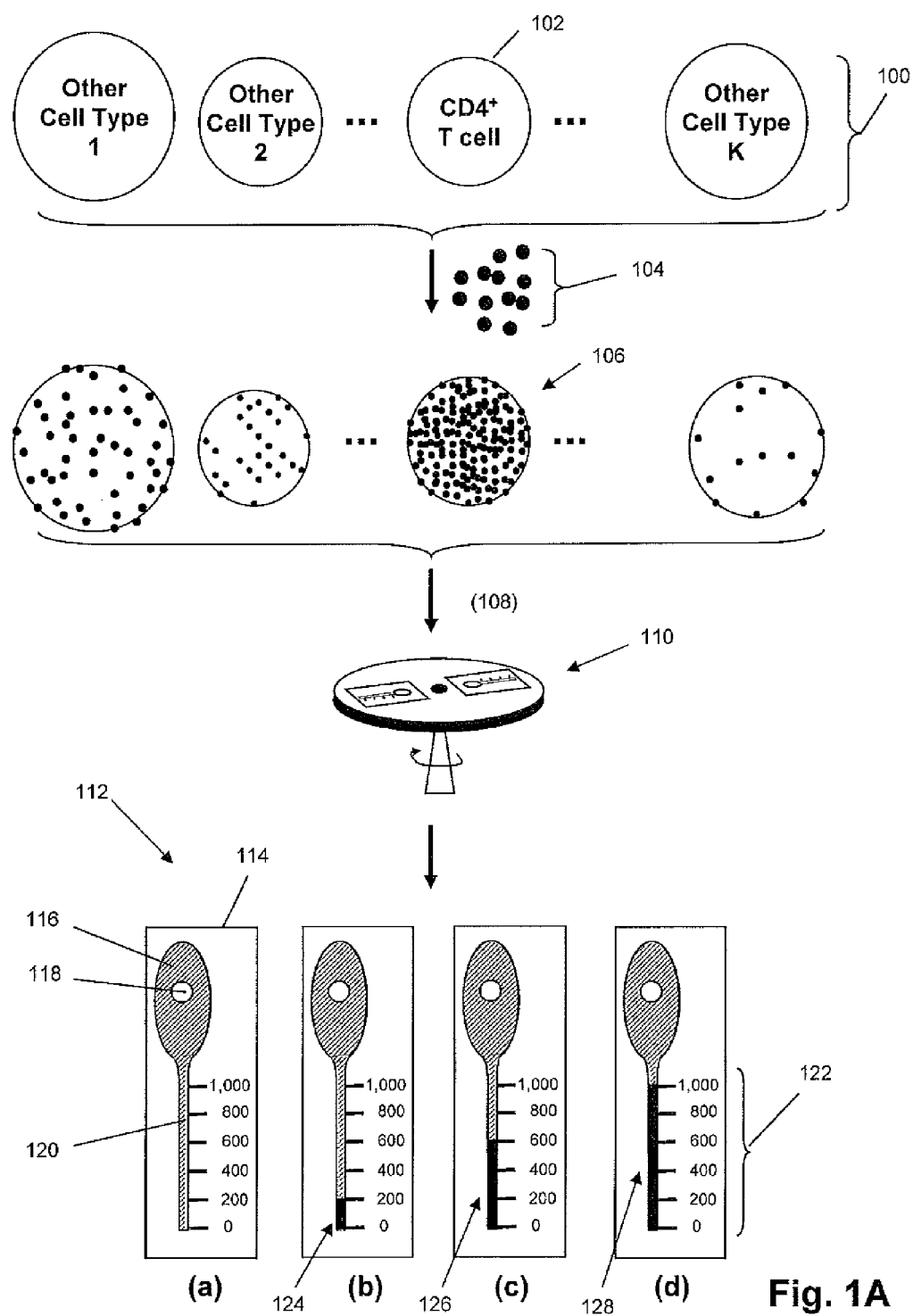
FIG. 1A illustrates the operation of one embodiment of the invention.

The practice of the present invention may employ, unless otherwise indicated, conventional techniques from molecular biology (including recombinant techniques), cell biology, immunoassay technology, microscopy, and analytical chemistry, which are within the skill of the art. Such conventional techniques include, but are not limited to, detection of fluorescent signals, image analysis, selection of illumination sources and optical signal detection components, selecting antibodies for specific cellular or molecular targets; labeling of biological cells, and the like. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press); Wild, Editor, The Immunoassay Handbook, Third Edition (Elsevier Science, 2005); Murphy, Fundamentals of Light Microscopy and Electronic Imaging (Wiley-Liss, 2001); Shapiro, Practical Flow Cytometry, Fourth Edition (Wiley-Liss, 2003); Herman et al, Fluorescence Microscopy, $2^{nd}$ Edition (Springer, 1998); all of which are herein incorporated in their entirety by reference for all purposes.

In one aspect, the invention provides a low-cost and convenient method for detecting certain cell types in a sample by separating them from other cell types using density labels, such as gold particles. Preferably, such labels are attached to the selected cell type by one or more antibodies specific for characteristic cell surface markers. The labeled cells are separated from other cells in the sample by centrifugation, sedimentation, or like technique, to form a distinct peak in a separation profile, which preferably can be discerned by direct inspection.

Successful detection in accordance with the invention depends on several factors, including (1) the types and numbers of cell surface markers on the desired cell type and on the other (undesired) types of cells in a sample, (2) the specificities and affinities of the binding compounds used with the density labels, (3) the size and composition of the density labels, (4) the magnitude of the centrifugal force used to separate the labeled and unlabeled cells of a sample, or whether sedimentation is employed for such purpose, and (5) the method of cell detection employed. In part, the invention includes the determination of cell types that can be successfully detected based on choices of the above factors. In one aspect, desired cell types (that is, the subset sought to be detected or quantified in a sample) are distinguished from undesired cell types by having at least thirty thousand selected cell surface markers in excess of undesired cell types; preferably, desired cell types have at least fifty thousand such cell surface markers; in further preference, desired cell types have at least seventy thousand such cell surface markers; and in still further preference, desired cell types have at least one hundred thousand such cell surface markers. The nature of cell surface markers employed (and their associated antigenic determinants) can vary widely depending on the cell type to be detected and the sample. Cell types of particular interest are hematopoietic cells and their various subdivisions, including but not limited to, myeloid cells, lymphoid cells, lymphocytes, monocytes, basophils, neutrophils, eosinophils, granulocytes, leukocytes, megakaryocytes, stem cells, and the like, and subsets of such subdivisions of cells. Cell surface markers employed to detect such cell types may be selected from well know CD molecules. In one aspect, cell surface markers for use with the invention are selected from the following set of CD and other molecules: CD2, CD3, CD4, CD5, CD7, CD8, CD11a, CD11b, CD11c, CD13, CD14, CD16, CD18, CD19, CD20, CD21, CD22, CD23, CD24, CD25, CD28, CD33, CD37, CD38, CD44, CD45, CD45RA, CD45RO, CD54, CD55, CD57, CD58, CD69, HLA-DR, and HLA Class 1. As mentioned above, desired cell types may be detected or quantified using one cell surface marker or a plurality of cell surface markers. When a plurality of cell surface markers is used, a binding compound specific for each different cell surface marker of the plurality is selected. Each such binding compound is then labeled with a density label (which may be the same or different), and is combined with the others to form a probe for use with the invention. An exemplary plurality of cell surface markers for particular desired cell types includes CD3 and CD33 for myloid cells. Of particular interest are cell types that express CD4 molecules, which may be used to assess or monitor the level of helper T cells in the blood of individuals inflected with HIV. Guidance for selecting cell types having cell surface markers for detection and quantification in accordance with the invention can be found in many references in the cytometry field, including the following: Bikoue et al, Cytometry 26: 137-147 (1996); Denny et al, Cytometry 6(suppl.):58 Abstract 55C (1993); Lenkei et al, J. Immunol. Meth. 183: 267-277 (1995); Poncelet et al, Cytometry 6(suppl): 60 Abstract 83C (1993); and the like, which are incorporated herein by reference.

Figure 1B:
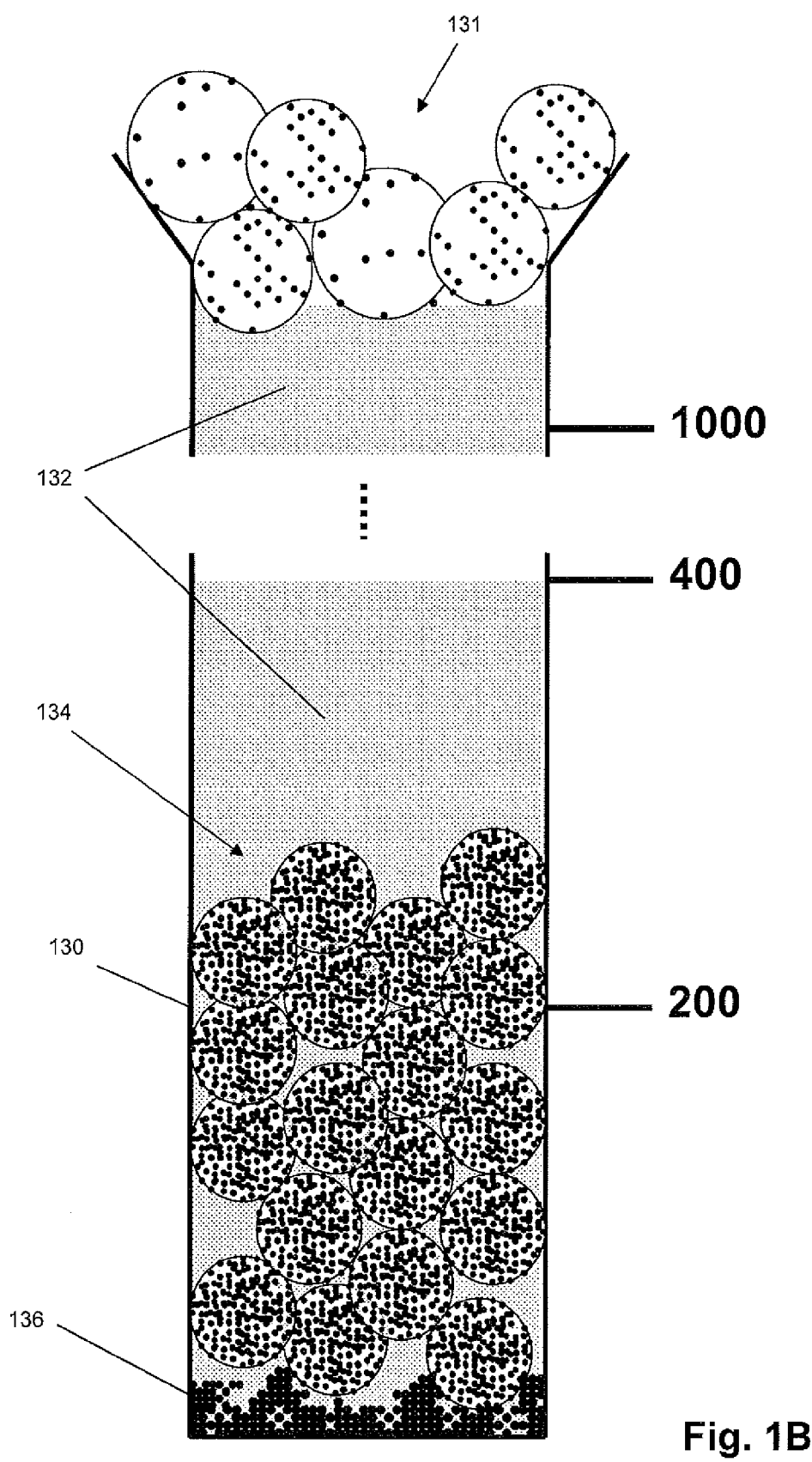
FIG. 1B illustrates how a readout is obtained with one embodiment of the invention.

The concept of the invention is illustrated in the embodiment of FIG. 1, where a method and device for detecting and measuring CD4-positive T cells in a sample is shown diagrammatically. Sample (100), which may contain multiple cell types as well as a subpopulation of desired cell types, is combined with probe (104) that typically comprises one or more density-labeled antibodies specific for one or more cell surface markers characteristic of cells of the desired subpopulation. Density labels can vary widely. Preferably, density labels are capable of being attached to a binding compound, such as an antibody or antibody fragment, to form a probe. In one aspect, density labels are metal particles or colloids, which may, for example, have sizes in the range of from 1 to 500 nm, or from 10 to 300 nm, or from 100 to 300 nm. Compositions of such metal particles may be gold, silver, platinum, tungsten, nickel, palladium, uranium, or the like, or alloys thereof. In particular, gold particles are preferred because of their high density, availability in a variety sizes and shapes, and availability of attachment chemistries. Exemplary references teaching the use of gold or silver particles with antibodies include Ribrioux et al, J. Histochem Cytochem 44: 207-213 (1996); Hayat et al, editors Immunogold-silver staining: principles, methods and applications (CRC Press, Boca Raton, 1995); and the like. Such probes are also commercially available, e.g. Nanoprobes (Stony Brook, N.Y.); BBInternational (Cardiff, UK); or the like. After incubation with the probe, cells of the sample are labeled to different degrees; that is, they carry different amounts of density-labeled probe. An important factor of the invention is that cells of the desired subpopulation (106) carry enough label so that they are denser than a predetermined density medium and that other cells of the sample remain less dense than the density medium, so that when the labeled cells are centrifuged through the density medium, or allowed to sediment, the cells of the desired subpopulation are separated from the rest of the cells in the sample. In one aspect, the sample may be combined with the probe in a disposable cuvette (112), illustrated in FIG. 1 and FIGS. 3A and 3B. In FIG. 1A, cuvette (112) is shown under four different conditions, (a)-(d). Each of the cuvettes shown comprises body (114) which contains chamber (116). Sample is loaded into chamber (116) through port, or opening, (118), after which it is combined with a probe with a density label, which may be pre-loaded into chamber (116), e.g. as a dried reagent or controlled release reagent. Preferably, chamber (116) is loaded with a predetermined volume of sample so that absolute cell counts may be made. In one embodiment, chamber (116) has a constant volume and is completely filled when a sample is taken or loaded. After incubation, cuvette (112) is inserted or loaded onto a centrifuge device, such as the one illustrated in FIG. 1A or FIG. 2, and sufficient centrifugal force is applied so that free density label and labeled cells of the desired subpopulation accumulate at the bottom of capillary (120), which is in fluid communication with chamber (116). The capillary, as exemplified by (120), may have a variety of cross-sectional area or geometries. In one aspect, it has a circular geometry with an inside diameter, or bore, in the range of from 0.025 mm to 3.5 mm. Alternatively, cuvette (112) may be fabricated as a microfluidics device wherein capillary (120) is a channel etched in a body, e.g. glass, plastic, or the like, using conventional microfluidic device manufacturing techniques. In FIG. 1A, capillary (120) is shown as being loaded with density medium (black fill), whereas in FIG. 3B, capillary (120) is shown empty. The top of cuvette (112) may include scale (122) associated with capillary (120) that gives a measure of cell numbers of the desired subpopulation after centrifugation is complete. When the density label is gold, or like metal, visualization of the column of labeled cells may be improved by pre-filling capillary (120) with a darkened solution, e.g. an ink or black neutral carbon solution, which is displaced during centrifugation or sedimentation by the labeled cells. FIG. 1B illustrates how such a scale provides a measure of cell number. End of capillary (130) is shown with density medium (132), accumulated free density label (136), and stack (134) of labeled cells of the desired subpopulation. As centrifugation proceeds, labeled cells accumulate at the bottom of capillary (130) so that stack (134) of labeled cells forms. The undesired cell types (131) that are less dense that the desired cell types do not penetrate density medium (132) and remain at the top of capillary (120). In one embodiment of the cuvette, the height of stack (134) can be inspected and converted into cell numbers or density by comparison with an inscribed scale, which in FIG. 1B is partially shown. As illustrated in FIG. 1A, conditions may exist where a sample contains different numbers of a cell type of interest, such as conditions corresponding to (a), (b), (c), and (d) of the figure. Where no cells of the desired subpopulation are present (condition (a)), then no stack of labeled cells is observed. Where conditions are such that increasing numbers of cells of the desired subpopulation are present (conditions (b) through (d)), then stacks of increasing heights are observed (124, 126, and 128). Selection of the dimensions of capillary (120), density labels, density medium, scale, chamber volume, and so on, are design choices that are selected for particular embodiments and applications. Preferably, a density label not only allows cell separation, but also permits visual inspection of the accumulation of labeled cells as a stack at the bottom of a capillary.

Figure 2:
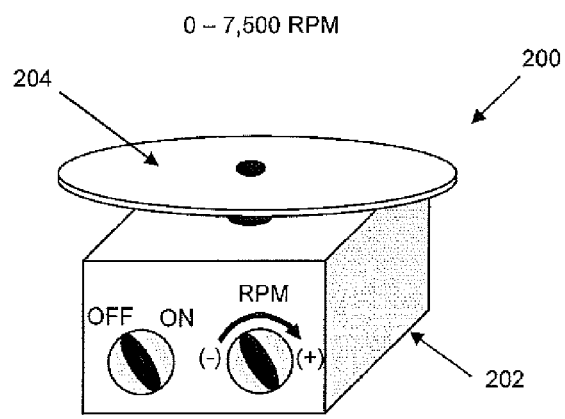
FIG. 2 is a photograph showing an apparatus for separating labeled cells by centrifugation in accordance with one embodiment of the invention.
Figure 3A:
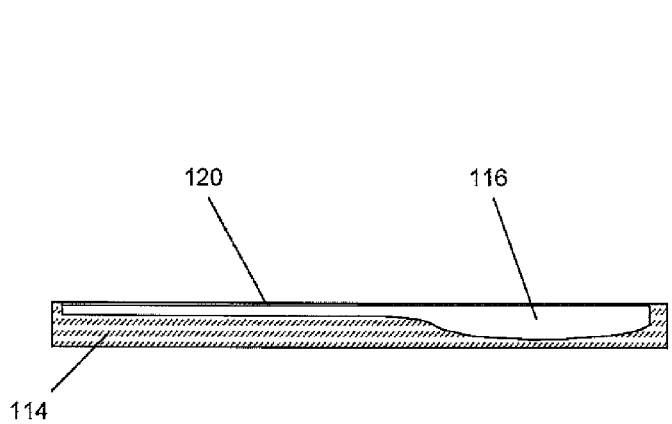
FIGS. 3A-3B illustrates exemplary cuvette and capillary apparatus for holding blood samples to be assayed by the method of the invention.
Figure 3B:
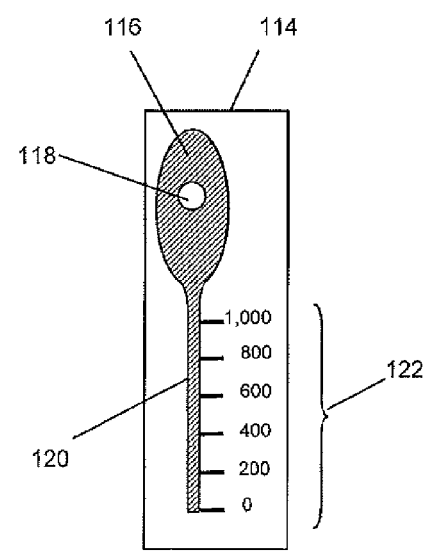

In one aspect, centrifugation of cuvettes may be carried out on a low-cost centrifuge (110), a prototype (200) of which is shown in FIG. 2. Prototype (200) comprises a motor in housing (202) that drives platform (204), onto which cuvettes are mounted.

Figure 4:
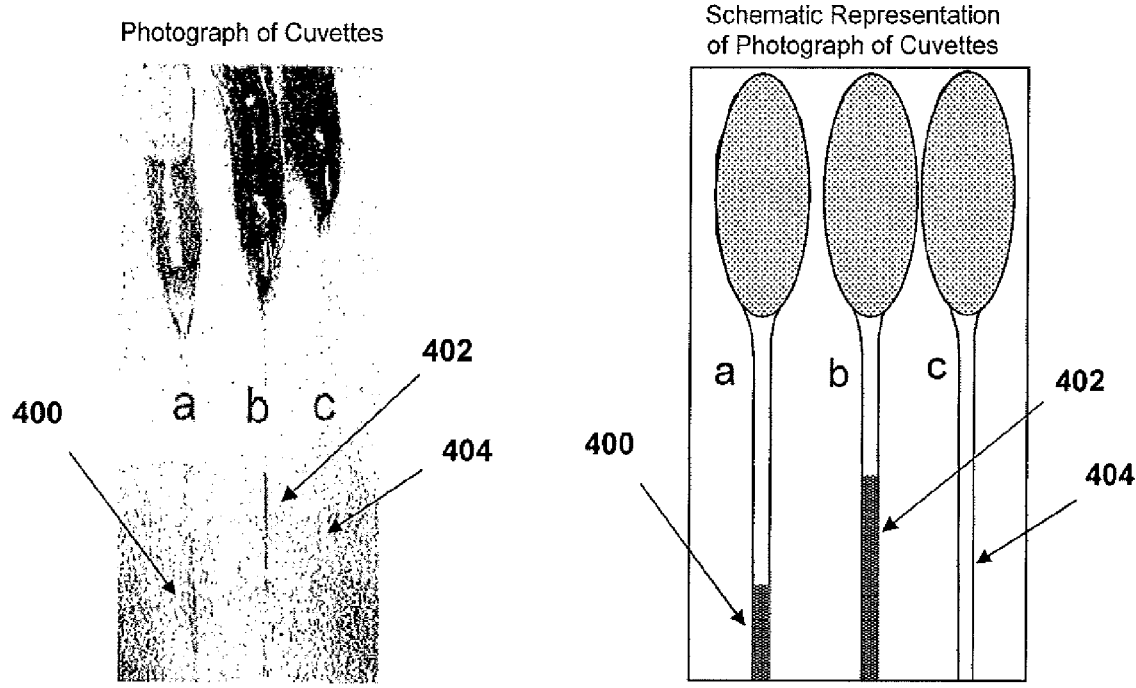
FIG. 4 shows cells separated by a method of the invention in a prototype apparatus.

In an embodiment of the method, a probe comprising gold-labeled anti-CD4 antibody was used to detect CD4-positive cells in whole blood. Probe was prepared as follows: To a reaction tube, 7 mL of 80 nm colloidal gold particles suspended in distilled water (BBInternational, Cardiff, UK, part no. EMGC80) was combined with 0.850 mL of 13.3 mg/mL anti-CD4 antibody (Leu3a) (Becton Dickinson, San Diego, Calif.) and incubated with gentle rotating overnight at 4° C. During such incubation, anti-CD4 antibody was adsorbed onto the surface of gold colloid particles to form the probe. (Alternatively, and preferably, density labels are covalently linked to antibodies using conventional techniques, e.g. Hermanson, Bioconjugate Techniques, Second Edition (Academic Press, 2008), whose disclosure of colloidal gold conjugations are incorporated by reference). Separately, to three microfuge tubes labeled (a), (b) and (c) is added 20 uL of 10% NaN3, after which to tube (a) is added 200 uL of plasma (prepared by spinning the whole blood at 15,000 rpm for 10 min), and to each of tubes (b) and (c) is added 100 uL of whole blood. After such additions, to each of tubes (a) and (b) is added 170 uL of 2 mg/mL 80 nm gold-labeled anti-CD4 antibody ("GB"), and to tube (c) is added 170 uL of 1× phosphate buffered saline (1×PBS), after which each reaction mixture is added to a separate cuvette with its capillary pre-filled with 40% Histodenz (Sigma). Each cuvette was then spun for 3 min at 5000-7500 rpm on the apparatus shown in FIG. 2. FIG. 4 contains a photograph of the three cuvettes that were loaded as described above with either (a) probes comprising CD4-specific antibodies with gold particles attached ("GB") and buffer, (b) whole blood ("WB") and probes, and (c) whole blood and buffer, but no probe.

In (a), probe (400) accumulates at the bottom of the capillary of the cuvette; in (b) labeled cells accumulate in a stack (402) in the bottom half of the capillary of the cuvette; and in (c), no accumulation of either labeled cells or free label is seen in capillary (404) of the cuvette.

DEFINITIONS

Generally, terms used herein not otherwise specifically defined have meanings corresponding to their conventional usage in the fields related to the invention, including analytical chemistry, biochemistry, molecular biology, cell biology, microscopy, image analysis, and the like, such as represented in the following treatises: Alberts et al, Molecular Biology of the Cell, Fourth Edition (Garland, 2002); Nelson and Cox, Lehninger Principles of Biochemistry, Fourth Edition (W. H. Freeman, 2004); Murphy, Fundamentals of Light Microscopy and Electronic Imaging (Wiley-Liss, 2001); Shapiro, Practical Flow Cytometry, Fourth Edition (Wiley-Liss, 2003); and the like.

"Antibody" or "immunoglobulin" means a protein, either natural or synthetically produced by recombinant or chemical means, that is capable of specifically binding to a particular antigen or antigenic determinant. Antibodies are usually heterotetrameric glycoproteins of about 150,000 daltons, composed of two identical light (L) chains and two identical heavy (H) chains. "Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragment. The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins. Guidance in the production and selection of antibodies for use in immunoassays can be found in readily available texts and manuals, e.g. Harlow and Lane, Antibodies: A Laboratory Manual (Cold Spring Harbor Laboratory Press, New York, 1988); Howard and Bethell, Basic Methods in Antibody Production and Characterization (CRC Press, 2001); Wild, editor, The Immunoassay Handbook (Stockton Press, New York, 1994), and the like.

"Antigenic determinant," or "epitope" means a site on the surface of a molecule, usually a protein, to which a single antibody molecule binds; generally a protein has several or many different antigenic determinants and reacts with antibodies of many different specificities. A preferred antigenic determinant is a phosphorylation site of a protein.

"Binding compound" means a compound that is capable of specifically binding to a particular target molecule. Examples of binding compounds include antibodies, lectins, nucleic acids, aptamers, and the like, e.g. Sharon and Lis, Lectins, $2^{nd}$ Edition (Springer, 2006); Klussmann, The Aptamer Handbook: Functional Oligonucleotides and Their Applications (John Wiley & Sons, New York, 2006).

"Complex" as used herein means an assemblage or aggregate of molecules in direct or indirect contact with one another. In one aspect, "contact," or more particularly, "direct contact" in reference to a complex of molecules, or in reference to specificity or specific binding, means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" usually refers to a stable aggregate of two or more proteins. In one aspect, a "complex" refers to a stable aggregate of two proteins, such as an antibody specifically bound to an antigenic determinant of a target protein.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

"Sample" means a quantity of material from a biological, environmental, medical, or patient source in which detection or measurement of target cells, particles, beads, and/or analytes is sought. The term "sample" encompasses biological samples, e.g. a quantity of blood, a microbiological culture, or the like; environmental samples, e.g. a soil or water sample; medical samples or specimens, e.g. a quantity of blood or tissue; or the like. Preferably, a sample is a human blood sample. The terms "sample" and "specimen" are used interchangeably.

"Specific" or "specificity" in reference to the binding of one molecule to another molecule means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least thirty percent. Generally, molecules involved in a specific binding event have areas on their surfaces, and/or in the case of proteins in cavities, giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A method for measuring the number of cells in a subpopulation of cells in a sample, wherein cells of the subpopulation have characteristic numbers of one or more cell surface markers, the method comprising the steps of:

combining under probe-binding conditions a sample with a probe comprising at least one binding compound specific for at least one of the one or more cell surface markers and a particle that is in the range of 10 nm to 300 nm in size, thereby forming a reaction mixture containing labeled cells from the subpopulation and other cells, wherein the one or more cell surface markers are present in greater numbers on cells of the subpopulation than on other cells of the sample and wherein the one or more cell surface markers, and the particle size and composition are selected so that labeled cells of the subpopulation have a density that is greater than that of other cells of the sample;

separating labeled cells of the reaction mixture through a density medium disposed in a capillary having a bottom, so that said labeled cells from said subpopulation form a stack having a height from the bottom of the capillary and comparing the height of said stack to a scale to provide a measure of the number of cells in said subpopulation.

2. The method of claim 1, wherein said cells of said subpopulation are lymphocytes.

3. The method of claim 2 wherein at least one of said binding compounds of said probe is specific for CD4-positive cells.

4. The method of claim 1, wherein said particle comprises a metal selected from the group consisting of gold, silver, nickel, platinum, tungsten, uranium, palladium, and alloys thereof.

5. The method of claim 4 wherein said particle is a colloid gold particle.

6. The method of claim 4 wherein said step of separating includes centrifuging said labeled cells.

7. The method of claim 6 wherein said cells of said subpopulation are lymphocytes.

8. The method of claim 7 wherein said lymphocytes are CD4-positive lymphocytes and said probe includes a colloidal gold-labeled anti-CD4 antibody.

9. The method of claim 1, wherein said particle is an 80 nm gold particle.

\* \* \* \* \*